United States Patent [19]

Yamamoto

[11] Patent Number: 4,547,615
[45] Date of Patent: Oct. 15, 1985

[54] PROCESS FOR PRODUCING CONJUGATED DIOLEFINS

[75] Inventor: Haruhisa Yamamoto, Takaoka, Japan

[73] Assignee: Nippon Zeon Co. Ltd., Tokyo, Japan

[21] Appl. No.: 618,922

[22] Filed: Jun. 8, 1984

[30] Foreign Application Priority Data

Jun. 16, 1983 [JP] Japan ............................... 58-108281
Oct. 26, 1983 [JP] Japan ............................... 58-200624

[51] Int. Cl.$^4$ ........................... C07C 5/48; C07C 5/09
[52] U.S. Cl. .................... 585/621; 585/622; 585/624; 585/625; 585/626; 502/305
[58] Field of Search ............... 585/621, 622, 624, 625, 585/626; 502/305

[56] References Cited

U.S. PATENT DOCUMENTS

| | | | |
|---|---|---|---|
| 3,801,670 | 4/1974 | Shiraishi et al. | 585/621 |
| 3,825,502 | 7/1974 | Takenaka et al. | 585/624 |
| 3,932,551 | 1/1976 | Grasselli et al. | 585/624 |
| 4,311,611 | 1/1982 | Sasaki et al. | 585/626 |
| 4,423,281 | 12/1983 | Yamamoto et al. | 585/626 |

Primary Examiner—D. E. Gantz
Assistant Examiner—Chung K. Pak
Attorney, Agent, or Firm—Sherman & Shalloway

[57] ABSTRACT

A process for producing a conjugated diolefin, which comprises oxidatively dehydrogenating a monoolefin having at least 4 carbon atoms in the vapor phase with molecular oxygen to form the corresponding conjugated diolefin, said reaction being carried out in the presence of a catalyst having the general composition formula

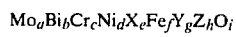

$$Mo_aBi_bCr_cNi_dX_eFe_fY_gZ_hO_i$$

wherein X represents Zr or Al, Y represents at least one element selected from the group consisting of metal elements of Group Ia of the periodic table, metal elements of Group II of the periodic table, Tl and P, Z represents at least one element selected from the group consisting of In, Ag, Ti, Nb, Ta, Co, La, Ce, Nd and Mn, a, b, c, d, e, f, g, h and i are respectively the atomic numbers of Mo, Bi, Cr, Ni, X, Fe, Y, Z and O, and when a=12, b=0.05–20, c=0.05–20, d=0.1–30, e=0.01–20, f=0.01–20, g=0.001–20, h=0–20, and i is the atomic number of oxygen satisfying the atomic valences of the other elements.

11 Claims, No Drawings

PROCESS FOR PRODUCING CONJUGATED DIOLEFINS

This invention relates to a process for producing a conjugated diolefin by oxidative dehydrogenation. More specifically, this invention relates to a process for producing a conjugated diolefin efficiently by oxidatively dehydrogenating a monolefin having at least 4 carbon atoms with molecular oxygen in the vapor phase in the presence of a novel catalyst.

Methods have been known which comprise oxidatively dehydrogenating a monolefin having at least 4 carbon atoms such as n-butene or isopentene in the vapor phase in the presence of a catalyst to produce a conjugated diene (i.e., 1,3-butadiene or isoprene) corresponding to the monolefin.

Specific examples of the catalyst used in such prior art techniques include multi-components catalysts containing molybdenum, bismuth and iron as essential components (for example, those disclosed in U.S. Pat. Nos. 3,764,632, 3,801,670 and 3,932,551), multi-component catalysts containing molybdenum, bismuth and chromium as essential components (for example, those disclosed in U.S. Pat. No. 3,956,181), and multi-component catalysts containing molybdenum, bismuth and zirconium as essential components (for example, those disclosed in Japanese Laid-Open Patent Publication No. 93793/1976). When these catalyst systems are applied to an isomeric mixture of monolefins industrially available at low cost, the yield of the desired conjugated diolefin is drastically reduced because with these catalysts, there is a great difference in reactivity among the monolefin isomers.

The present inventors made a great deal of efforts in developing a catalyst which would not cause such a difference in reactivity among any starting monolefin isomers, and found that some catalysts being free from iron and containing molybdenum, bismuth and chromium as essential components are effective (for example, U.S. Pat. Nos. 4,423,281 and 4,336,409).

On further investigation, the present inventor found new problems to be solved. For example, when these catalysts are used, the reaction temperature should be somewhat higher, and the reactor must be made of a material of a higher cost. Furthermore, when the reaction is continued for a long period of time, high-boiling by-products tend to block up the reaction system.

It is an object of this invention therefore to provide an improvement in the process for producing a conjugated diolefin by oxidatively dehydrogenating a monolefin having at least 4 carbon atoms with molecular oxygen in the vapor phase by developing a catalyst which hardly brings about any difference in reactivity among starting monolefin isomers, can give the desired conjugated diolefin efficiently at lower temperatures, and does not form high-boiling by-products even when used for a long period of time.

According to this invention, there is provided a new catalyst which meets the aforesaid object and which is represented by the general composition formula

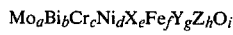

$Mo_aBi_bCr_cNi_dX_eFe_fY_gZ_hO_i$ wherein X represents Zr or Al, Y represents at least one element selected from the group consisting of metal elements of Group Ia of the periodic table, metal elements of Group II of the periodic table, Tl and P, Z represents at least one element selected from the group consisting of In, Ag, Ti, Nb, Ta, Co, La, Ce, Nd and Mn, a, b, c, d, e, f, g, h and i are respectively the atomic numbers of Mo, Bi, Cr, Ni, X, Fe, Y, Z and O, and when a=12, b=0.05–20, preferably 0.1–8, c=0.05–20, preferably 0.1–10, d=0.1–30, preferably 1–20, e=0.01–20, preferably 0.05–10, f=0.01–20, preferably 0.05–5, g=0.001–20, preferably 0.01–10, h=0–20, preferably 0.01–10, i is the atomic number of oxygen satisfying the atomic valences of the other elements.

The starting materials used in this invention may be any monolefins having at least 4 carbon atoms which have heretofore been used to synthesize conjugated dienes by oxidative hydrogenation. Specific examples include butene-1, butene-2, pentene-1, pentene-2, 2-methylbutene-1, 2-methylbutene-2, 3-methylbutene-1, 2,3-dimethylbutene-1 and 2,3-dimethylbutene-2. These monolefins need not to be used in isolated form, and as required may be used in an arbitrary mixture. For example, when it is desired to obtain 1,3-butadiene, highly pure butene-1 or butene-2 may be used as a starting material. But a fraction containing butene-1 and butene-2 as main components (to be referred to as BBRR) obtained by separating 1,3-butadiene and isobutylene from a $C_4$ fraction obtained as a by-product in the cracking of naphtha, or a butene fraction formed by dehydrogenation or oxidative dehydrogenation of n-butene may also be used. In the latter case, too, the same yield as in the case of using a single material of high purity can be obtained. To obtain isoprene or 1,3-pentadiene, a fraction containing isopentene as a main component or a fraction containing n-pentene as a main component may similarly be used. The use of a $C_5$ monoolefin fraction containing isopentene and n-pentene as main components as the starting material can simultaneously give isoprene and 1,3-pentadiene.

The compositional characteristic of the catalyst used in this invention is that zirconium or aluminum is selected from the component Z of the known Mo—Bi—Cr—Ni—Y—Z catalyst disclosed in U.S. Pat. No. 4,423,281 and used as the component X, and iron excluded in the prior art is combined and thus chromium, nickel, the component X and iron are used as essential components. If any one of chromium, nickel and the component X is lacking, it is impossible to remove the difference in reactivity among the monolefin isomers, and moreover to inhibit the formation of high-boiling by-products.

When the catalyst does not contain iron, the reaction temperature at which the same catalytic performance (the yield of the diolefin) as the catalyst of the invention is obtained becomes higher and the amount of high-boiling by-products increase, although scarcely any difference in reactivity among the monolefin isomers is observed.

The component Y is also an essential component of the catalyst of this invention, and if it is absent, the reaction becomes unstable and the reactivity of the starting material is reduced.

The component Z is not essential, but can serve to reduce the formation of high-boiling by-products. The individual elements of the component Y or the component Z exhibit equivalent effects. Particularly when K, Rb, Ca, Tl, Ba, Zn, Cd and P are used as the component Y and In, Nd and Mn are used as the component Z, a catalyst having especially superior performance can be obtained. The individual elements of the component X, the component Y or the component Z need not always to be used singly, and two or more of them may be used in combination.

The catalyst used in this invention may be prepared by methods known in the art, for example by evaporation-drying, oxide mixing or co-precipitation. Starting materials for the individual elements which are used in the preparation of the catalyst may be any compounds which can give the catalyst of this invention by calcination. Examples include salts such as ammonium salts, nitrates, carbonates, organic acid salts and halides; free acids, acid anhydrides, fused acids; molybdenum-containing heteropolyacids such as phosphomolybdic acid and silicomolybdic acid; and salts such as ammonium salts and metal salts of heteropolyacids.

Calcination for the purpose of preparing the catalyst from the raw materials or of activating the catalyst, is carried out usually at 300° to 900° C., preferably 450° to 700° C., for about 4 hours to about 16 hours while passing a gas containing molecular oxygen. As required, a primary calcination treatment may be carried out at a temperature below the aforesaid calcination temperature, and then the calcination treatment is carried out at the above temperature.

The catalyst of this invention may be prepared, for example, by adding an aqueous solution of salts of the component Y element, chromium, nickel, bismuth, the component X element, iron and the component Z element to an aqueous solution of ammonium molybdate, adjusting the mixed solution to a pH in the range of 2 to 9 with an aqueous solution of ammonia or an aqueous solution of nitric acid, stirring the solution, drying the resulting muddy suspension after, as required, adding a suitable carrier material, drying the resulting cake-like material in the air, and then calcining it at the aforesaid calcination temperature.

The catalyst of this invention may be directly used. Alternatively, it may be used deposited on a carrier of a suitable shape, or diluted with a carrier (diluent) in the form of a sol or gel. Examples of the carrier or diluent are titanium dioxide, silica gel, silica sol, diatomaceous earth, silicon carbide, inert alumina, pumice, silica alumina, bentonite, zeolite, talc, and refractories which are known. Silicon-containing carriers are preferred. The amount of the carrier may be properly chosen. The catalyst may be used in any of a fixed bed method, a moving bed method and a fluidized bed method either as a powder or as tablets of a suitable shape.

The reaction of the monolefin with molecular oxygen in the process of this invention is carried out in a customary manner except that the aforesaid novel catalyst is used. For example, the source of supplying molecular oxygen needs not always be highly pure oxygen, and rather, air is practical in industrial practice. As required, the molecular oxygen may be diluted with an inert gas which does not adversely affect the reaction (for example, waste gases obtained by removing steam, nitrogen, argon, carbon dioxide gas, useful hydrocarbons, etc. from the reaction product). The reaction temperature is 250° to 700° C., preferably 300° to 600° C. The reaction pressure is atmospheric pressure to 10 atomspheres. The space velocity (SV) of the entire starting gas is 200 to 10,000 hr$^{-1}$, preferably 300 to 6,000 hr$^{-1}$ (at NTP). The concentration of the monolefin in the feed gas is from 0.1 to 40% by volume. The ratio of the monolefin to oxygen is 1:0.1-7. The preferred mole ratio of the monolefin, air, and steam in the feed gas is 1:2-30:0-50.

According to the process of this invention, the corresponding conjugated diolefin can be efficiently synthesized from the monolefin; for example, 1,3-butadiene, isoprene, 1,3-pentadiene and 2,3-dimethylbutadiene can be obtained from n-butene, isoprene, n-pentene and 2,3-dimethylbutene. The catalyst used in this invention scarcely causes a difference in reactivity among the monolefin isomers, and does not undergo a reduction in activity by paraffins. Accordingly, it is particularly suitable when the starting material is a fraction industrially available at low cost, such as an isomeric mixture of monolefins, or a mixture of it with paraffins. In this case, too, the conjugated diolefins can be obtained in yields equivalents to those obtained by using a monolefin composed of a single isomer as a starting material. The catalyst used in this invention has a long life, does not form too much high-boiling substances which may block up a pipe at the exit of a reactor, nor does it adversely affect the catalytic activity even when its strength is increased. With the catalyst of this invention, therefore, the reaction can be carried out stably over an extended period of time, and moreover even when the concentration of the monolefin and the space velocity are increased, the decrease in the yield of the desired conjugated diene is little.

The following examples illustrate the present invention more specifically. In these examples, the conversion, selectivity and one-pass yield were calculated in accordance with the following equations. In performing the calculation, if the monolefin used as a starting material contains the corresponding conjugated diolefin, the amount of this conjugated diolefin is substracted from the amount of the final conjugated diolefin obtained. Furthermore, a partially isomerized monolefin is dealt with as the unreacted monolefin.

$$\text{Reaction conversion of monolefin (\%)} = \frac{\text{Moles of monolefin reacted}}{\text{Moles of monolefin fed}} \times 100$$

$$\text{One-pass yield of diolefin (\%)} = \frac{\text{Moles of the corresponding diolefin formed}}{\text{Moles of monolefin fed}} \times 100$$

$$\text{Selectivity of diolefin (\%)} = \frac{\text{Moles of the corresponding diolefin formed}}{\text{Moles of monolefin reacted}} \times 100$$

The amount of the high-boiling by-products was measured in the following manner. A copper pipe 8 mm in inside diameter and 3 m in length was fitted to the exit of a reaction tube, and maintained at 95° C. using a hot water bath. The reaction gas was passed through the reaction tube for 100 hours, and thereafter, the copper pipe was dried at room temperature under reduced pressure until no change in the weight of the copper pipe was noted. The balance obtained by subtracting the previously measured weight of the copper tube from the resulting weight is defined as the amount of the high-boiling by-products.

EXAMPLE 1

Bismuth nitrate (48.5 g), 26.7 g of zirconyl nitrate, 4.04 g of ferric nitrate, 232.6 g of nickel nitrate, 45.6 g of chromium nitrate and 2.02 g of potassium nitrate were added to 150 ml of water, and heated to form a solution (designated as solution A). Ammonium molybdate (212 g) was dissolved in 400 ml of hot water to form a solution (designated as solution B).

The solution A was fully stirred under heat, and then the solution B was added. The mixture was vigorously stirred, adjusted to pH 5 with a 3% by weight aqueous solution of ammonia, left to stand at room temperature for 50 hours, and evaporated to dryness over an oil bath. The residue was dried at 120° C. for 8 hours, primarily calcined in air at 350° C. for 4 hours, and then pulverized to a size of 100 mesh or smaller. The pulverized calcination product was mixed with 40% by weight thereof of a silicon carbide powder (1500 mesh or smaller) and 3% by weight thereof of silica (20% by weight of silica sol). Furthermore, a suitable amount of a lubricant (a hot aqueous solution of ethylene glycol and methyl cellulose) was added, and the mixture was kneaded by a mixing and grinding machine until it became sufficiently uniform. The mixture was extrusion-molded into pellets having a diameter of 3 mm and a length of 1 cm and dried at 120° C. for 16 hours.

The pellets were calcined at 400° C. for 2 hours and then at 570° C. for 6 hours in a stream of air. The resulting catalyst (catalyst No. 1) excepting oxygen and the carrier, had the following elemental composition.

$$Mo_{12}Bi_1Cr_3Ni_8Zr_1Fe_{0.1}K_{0.2}$$

One hundred milliliters of the resulting catalyst was filled in a stainless steel reaction tube having an inside diameter of 2.5 cm and a length of 60 cm, and heated to 310° C. by a metal bath. Each of the starting hydrocarbons indicated in Table 1 was passed through the catalyst layer so that the flow rate of n-butene contained in it became 18 liters (gaseous, at NTP) per hour and the flow rate of air became 132 liters (at NTP) per hour. The results obtained after 5 hours from the start of the reaction are shown in Table 2.

It is seen from the results given in Table 2 that when the catalyst of this invention is used, there is hardly any difference in reactivity between butene-1 and butene-2, and 1,3-butadiene is formed in a high yield. Furthermore, even when BBRR industrially available at low cost in large amounts is used as the starting material, the yield is equivalent to the case of using highly pure butene. This is quite a unique phenomenon. Furthermore, the amount of high-boiling by-products is small, and during the collection of these high-boiling by-products, no trouble by the blocking of the pipe was observed with any of the starting materials.

TABLE 1

| Components (mole %) | Starting hydrocarbon | | | | | |
|---|---|---|---|---|---|---|
| | Butene-1 | trans-Butene-2 | cis-Butene-2 | n-Butene | BBRR-1 | BBRR-2 |
| Ethane | | | | | 0.16 | 0.07 |
| Propane | | | | | 0.05 | 0.11 |
| Propylene | | | | | 0.02 | 0.07 |
| Allene | | | | | 0.02 | |
| Cyclopropane | | | | | 0.03 | |
| iso-Butane | 0.20 | | | 0.38 | 12.38 | 11.58 |
| n-Butane | 0.38 | 0.21 | | 0.41 | 12.95 | 28.13 |
| Butene-1 | 96.22 | | | 44.66 | 39.45 | 10.01 |
| iso-Butene | 0.05 | | | 0.11 | 0.44 | 3.74 |
| trans-Butene-2 | 0.61 | 99.00 | 0.18 | 27.33 | 19.71 | 30.80 |
| cis-Butene-2 | 1.93 | 0.51 | 99.75 | 26.64 | 12.32 | 9.76 |
| 1,3-Butadiene | 0.61 | 0.28 | 0.07 | 0.47 | 0.10 | 1.11 |
| C5 or higher | | | | | 2.07 | 3.62 |
| Others | | | | | 0.30 | 1.00 |
| Total | 100.00 | 100.00 | 100.00 | 100.00 | 100.00 | 100.00 |

TABLE 2

| Run No. | Starting hydrocarbon | Conversion of n-Butane (%) | Yield (selectivity) of 1,3-butadiene (%) | Amount of high-boiling by-products (g) |
|---|---|---|---|---|
| 1-1 | Butene-1 | 93.8 | 86.9 (92.6) | 0.90 |
| 1-2 | trans-Butene-2 | 93.0 | 86.2 (92.7) | 0.89 |
| 1-3 | cis-Butene-2 | 93.0 | 86.5 (93.0) | 0.91 |
| 1-4 | n-Butene | 94.1 | 87.0 (92.5) | 0.90 |
| 1-5 | BBRR-1 | 93.5 | 85.6 (91.6) | 0.91 |
| 1-6 | BBRR-2 | 92.8 | 85.4 (92.0) | 1.03 |

EXAMPLE 2

The catalysts (Nos. 2 to 19) shown in Table 3 were prepared in accordance with the procedure of Example 1 using various elements of the component Y instead of potassium and varying the composition of the catalyst. For phosphorus, 85% phosphoric acid was used as a raw material, and for the other elements of component Y, the corresponding nitrates were used as materials.

BBRR-1 shown in Table 1 was reacted in the same way as in Example 1 using each of the catalysts so prepared. The results obtained after 5 hours are shown in Table 3.

TABLE 3

| Run No. | Catalyst No. | Catalyst composition (atomic ratio) | Conversion of n-Butene (%) | Yield (selectivity) of 1,3-butadiene (%) | Amount of high-boiling by-products (g) |
|---|---|---|---|---|---|
| 2-1 | 2 | $Mo_{12}Bi_3Cr_3Ni_8Zr_2Fe_{0.1}Li_8$ | 86.4 | 77.5 (89.7) | 0.98 |
| 2-2 | 3 | $Mo_{12}Bi_{0.5}Cr_3Ni_8Zr_{0.5}Fe_1Na_1$ | 86.1 | 76.7 (89.1) | 0.96 |
| 2-3 | 4 | $Mo_{12}Bi_1Cr_3Ni_8Zr_1Fe_{0.2}Rb_{0.15}$ | 93.0 | 85.0 (91.4) | 0.91 |
| 2-4 | 5 | $Mo_{12}Bi_1Cr_2Ni_7Zr_1Fe_3Cs_{0.05}$ | 92.2 | 84.0 (91.1) | 0.93 |
| 2-5 | 6 | $Mo_{12}Bi_1Cr_3Ni_8Zr_2Fe_{0.1}Tl_{0.2}$ | 92.8 | 84.2 (90.7) | 0.96 |
| 2-6 | 7 | $Mo_{12}Bi_8Cr_{0.5}Ni_2Zr_4Fe_1P_{0.5}$ | 90.3 | 81.6 (90.4) | 0.94 |
| 2-7 | 8 | $Mo_{12}Bi_1Cr_{10}Ni_1Zr_1Fe_1Be_{15}$ | 82.6 | 72.3 (87.5) | 1.00 |

TABLE 3-continued

| Run No. | Catalyst No. | Catalyst composition (atomic ratio) | Conversion of n-Butene (%) | Yield (selectivity) of 1,3-butadiene (%) | Amount of high-boiling by-products (g) |
| --- | --- | --- | --- | --- | --- |
| 2-8 | 9 | $Mo_{12}Bi_1Cr_3Ni_3Zr_3Fe_1Mg_1$ | 85.6 | 76.0 (88.8) | 0.97 |
| 2-9 | 10 | $Mo_{12}Bi_1Cr_3Ni_4Zr_{0.1}Fe_5Ca_2$ | 85.1 | 75.7 (89.0) | 0.98 |
| 2-10 | 11 | $Mo_{12}Bi_1Cr_3Ni_{15}Zr_1Fe_{0.1}Sr_1$ | 84.9 | 76.0 (89.5) | 0.99 |
| 2-11 | 12 | $Mo_{12}Bi_1Cr_3Ni_8Zr_1Fe_{0.5}Ba_{0.5}$ | 92.9 | 84.9 (91.4) | 0.91 |
| 2-12 | 13 | $Mo_{12}Bi_1Cr_3Ni_6Zr_1Fe_{0.1}Cd_2$ | 92.5 | 83.9 (90.7) | 0.92 |
| 2-13 | 14 | $Mo_{12}Bi_1Cr_3Ni_7Zr_{1.5}Fe_{0.1}Zn_1$ | 92.2 | 84.1 (91.2) | 0.91 |
| 2-14 | 15 | $Mo_{12}Bi_1Cr_3Ni_8Zr_1Fe_{0.1}K_{0.1}Cs_{0.01}$ | 90.6 | 84.5 (93.3) | 0.88 |
| 2-15 | 16 | $Mo_{12}Bi_1Cr_3Ni_7Zr_1Fe_{0.2}Tl_{0.1}K_{0.1}$ | 92.8 | 84.9 (91.5) | 0.92 |
| 2-16 | 17 | $Mo_{12}Bi_1Cr_3Ni_7Zr_1Fe_1Rb_{0.1}P_{0.5}$ | 92.1 | 82.7 (89.8) | 0.96 |
| 2-17 | 18 | $Mo_{12}Bi_3Cr_3Ni_8Zr_1Fe_{0.5}K_{0.1}Cd_1$ | 93.3 | 83.6 (89.6) | 0.99 |
| 2-18 | 19 | $Mo_{12}Bi_3Cr_3Ni_7Zr_1Fe_{0.1}Ba_{0.5}Be_{10}$ | 88.7 | 77.8 (87.7) | 0.97 |

COMPARATIVE EXAMPLE 1

Catalysts Nos. (c-1) to (c-7) were prepared in the same way as in Example 1 except that in the preparation of catalyst No. 1 Cr, Ni, Zr or Fe component was not used.

Butene-1, trans-butene-2 and BBRR-1 were each reacted by the same method as in Example 1 using each of the resulting catalysts. The results obtained after 5 hours are shown in Table 4.

Furthermore, in the reactions catalyzed by these comparative catalysts, the copper pipe for collection of high-boiling by-products was blocked up more than three times, and every time the reaction had to be suspended.

EXAMPLE 3

A catalyst having the composition $Mo_{12}Bi_1Cr_3Ni_8Zr_1Al_eFe_{0.1}K_{0.2}Z_h$ was prepared in the same way as in Example 1 except that the component Al or Z was

TABLE 4

| | | Reaction of butene-1 | | | Reaction of trans-butene-2 | | |
| --- | --- | --- | --- | --- | --- | --- | --- |
| Comparative catalyst No. | Catalyst composition (atomic ratio) | Conversion of Butene-1 (%) | Yield (selectivity) of 1,3-butadiene (%) | Amount of high-boiling by-products (g) | Conversion of trans-Butene-2 (%) | Yield (selectivity) of 1,3-butadiene (%) | Amount of high-boiling by-products (g) |
| (c-1) | $Mo_{12}Bi_1Ni_8Zr_1Fe_{0.1}K_{0.2}$ | 49.2 | 37.8 (76.8) | 4.92 | 31.5 | 24.9 (79.0) | 3.88 |
| (c-2) | $Mo_{12}Bi_1Cr_3Zr_1Fe_{0.1}K_{0.2}$ | 32.6 | 26.2 (80.4) | 4.49 | 21.5 | 17.2 (80.0) | 4.40 |
| (c-3) | $Mo_{12}Bi_1Cr_3Ni_8Fe_{0.1}K_{0.2}$ | 73.6 | 60.9 (82.7) | 8.14 | 44.5 | 36.6 (82.2) | 7.71 |
| (c-4) | $Mo_{12}Bi_1Cr_3Ni_8Zr_1K_{0.2}$ | 71.9 | 65.6 (91.2) | 4.06 | 70.7 | 64.9 (91.8) | 4.05 |
| (c-5) | $Mo_{12}Bi_1Ni_8Fe_{0.1}K_{0.2}$ | 70.4 | 56.4 (80.1) | 7.78 | 52.3 | 42.6 (81.5) | 7.00 |
| (c-6) | $Mo_{12}Bi_1Cr_3Ni_8K_{0.2}$ | 67.8 | 57.2 (84.4) | 6.81 | 55.6 | 46.6 (83.8) | 6.47 |
| (c-7) | $Mo_{12}Bi_1Ni_8Zr_1K_{0.2}$ | 68.1 | 54.8 (80.5) | 6.51 | 48.2 | 39.1 (81.1) | 6.16 |

| | | Reaction of BBRR-1 | | |
| --- | --- | --- | --- | --- |
| Comparative catalyst No. | Catalyst composition (atomic ratio) | Conversion of n-Butene (%) | Yield (selectivity) of 1,3-butadiene (%) | Amount of high-boiling by-products (g) |
| (c-1) | $Mo_{12}Bi_1Ni_8Zr_1Fe_{0.1}K_{0.2}$ | 34.4 | 26.6 (77.3) | 5.67 |
| (c-2) | $Mo_{12}Bi_1Cr_3Zr_1Fe_{0.1}K_{0.2}$ | 26.9 | 21.5 (79.9) | 4.73 |
| (c-3) | $Mo_{12}Bi_1Cr_3Ni_8Fe_{0.1}K_{0.2}$ | 48.8 | 40.0 (82.0) | 8.56 |
| (c-4) | $Mo_{12}Bi_1Cr_3Ni_8Zr_1K_{0.2}$ | 71.3 | 65.2 (91.4) | 4.18 |
| (c-5) | $Mo_{12}Bi_1Ni_8Fe_{0.1}K_{0.2}$ | 59.9 | 48.2 (80.5) | 8.13 |
| (c-6) | $Mo_{12}Bi_1Cr_3Ni_8K_{0.2}$ | 61.3 | 48.5 (79.1) | 7.12 |
| (c-7) | $Mo_{12}Bi_1Ni_8Zr_1K_{0.2}$ | 54.8 | 44.1 (80.5) | 7.75 |

It is seen from the results obtained that if any one of Cr, Ni, Zr and Fe is lacking, the resulting catalyst has a drastically reduced performance, and large amounts of high-boiling by-products are formed. With the comparative catalysts other than the catalyst No. (c-4), the reactivity of butene-2 is much inferior to that of butene-1, and when BBRR industrially available in large quantities is used as a starting material, a satisfactory yield of butadiene cannot be obtained.

The comparative catalyst No. (c-4), as described in the specification of U.S. Pat. No. 4,423,281, shows an excellent performance when the temperature of the metal bath in the reactor is adjusted to 350° C. But when the temperature of the metal bath is set at 310° C. as in the present Comparative Example, the performance of the catalyst is drastically reduced.

additionally used. As raw materials for Nb and Ta, a fine powdery oxide of each was suspended in hot water and added to the solution A. For Si and Ti, an aqueous solution of the chloride was added to the solution A. For the other components Z, an aqueous solution of the nitrate was added to the solution A.

BBRR-1 was reacted by the same process as in Example 1 using each of the catalysts prepared. The results obtained after 5 hours are shown in Table 5.

TABLE 5

| Run No. | Catalyst No. | Catalyst composition (atomic ratio) $Al_c$ | Catalyst composition (atomic ratio) $Z_h$ | Conversion of n-butene (%) | Yield (selectivity) of 1,3-butadiene (%) | Amount of high-boiling by-products (g) |
|---|---|---|---|---|---|---|
| 3-1 | 20 | $Al_5$ | — | 93.0 | 85.5 (91.9) | 0.66 |
| 3-2 | 21 | — | $In_{0.1}$ | 92.1 | 84.8 (92.1) | 0.59 |
| 3-3 | 22 | — | $Ag_{0.5}$ | 94.1 | 85.9 (91.3) | 0.85 |
| 3-4 | 23 | — | $Si_1$ | 93.3 | 85.3 (91.4) | 0.62 |
| 3-5 | 24 | — | $Ti_2$ | 92.7 | 84.9 (91.6) | 0.83 |
| 3-6 | 25 | — | $Nb_{0.5}$ | 93.3 | 84.3 (90.4) | 0.79 |
| 3-7 | 26 | — | $Ta_{0.1}$ | 92.7 | 84.4 (91.0) | 0.80 |
| 3-8 | 27 | — | $Co_1$ | 92.4 | 85.0 (92.0) | 0.79 |
| 3-9 | 28 | — | $La_{0.1}$ | 93.7 | 83.8 (89.4) | 0.75 |
| 3-10 | 29 | — | $Ce_{0.5}$ | 93.4 | 83.1 (89.0) | 0.83 |
| 13-11 | 30 | — | $Nd_1$ | 92.8 | 85.1 (91.7) | 0.65 |
| 13-12 | 31 | — | $Mn_{0.5}$ | 93.8 | 85.5 (91.2) | 0.66 |
| 3-13 | 32 | $Al_1$ | $Co_{0.5}$ | 92.9 | 85.5 (92.0) | 0.65 |
| 3-14 | 33 | — | $Si_{10}Mn_2$ | 91.5 | 83.7 (91.5) | 0.62 |
| 3-15 | 34 | — | $Ag_{0.1}Ce_{0.1}$ | 92.2 | 82.6 (89.6) | 0.74 |

EXAMPLE 4

One hundred milliliters of the catalyst obtained in Example 1 was filled in a stainless steel reaction tube having an inside diameter of 2.5 cm and a length of 60 cm, and heated to 320° C. with a metal bath. A feed gas composed of BBRR-1, air and steam in a mole ratio of 15:35:32 was passed through the reaction tube with a contact time of 2 seconds (at NTP). The conversion of n-butene contained in BBRR-1 was 93.8%. The yield of 1,3-butadiene was 85.7%, and the selectivity of 1,3-butadiene was 91.4%. The amount of high-boiling by-products collected by the same method as in Example 1 was 0.65 g.

EXAMPLE 5

Example 4 was repeated except that instead of steam in the feed gas, a waste gas obtained by removing hydrocarbons from the reaction product gas was used. The waste gas contained nitrogen, unreacted oxygen, and by-product carbon monoxide or dioxide. The conversion of n-butene was 94.0%. The yield of 1,3-butadiene was 85.1%, and the selectivity of 1,3-butadiene was 90.5%. The amount of high-boiling by-products collected by the same method as in Example 1 was 1.32 g.

EXAMPLE 6

In the same way as in Run No. (1-5) in Example 1, the reaction was started, and continued for more than 100 hours to test the life of the catalyst. After the lapse of 2,000 hours, the conversion of n-butene in BBRR-1 was 92.2%, the yield of 1,3-butadiene was 85.1%, and the selectivity of 1,3-butadiene was 92.3%. This shows that the catalyst retained substantially the same activity as in the early stage of the reaction. The amount of high-boiling by-products was 0.85 g, which was smaller than that at the early stage of the reaction. The components or composition of BBRR-1 varied considerably every time the raw material was exchanged, but the reaction proceeded always stably and the results of the reaction were substantially constant.

COMPARATIVE EXAMPLE 2

The reactions of BBRR-1 in Comparative Example 1 with the comparative catalysts Nos. (c-1), (c-3) and (c-4) were continued for a long period of time. With any of these catalysts, the copper tube having an inside diameter of 8 mm at the exit of the reactor was frequently blocked up by high-boiling by-products, and the operation had to be stopped after 500 hours.

EXAMPLE 7

Instead of the n-butenes in Example 1, a hydrocarbon mixture having the composition shown in Table 6 and containing n-pentenes (pentene-1 and pentene-2) and isopentenes (3-methyl-butene-1, 2-methyl-butene-1 and methyl-butene-2) was used. The same reaction as in Example 1 was carried out except that a feed gas composed of 18 liters/hr (gaseous, at NTP) of n-pentene and isopentene combined and 132 liters/hr (at NTP) of air was used. The conversion of isopentene was 77.9%. The yield of isoprene was 67.1%, and the selectivity of isoprene was 86.1%. The conversion of n-pentene was 81.6%. The yield of 1,3-pentadiene was 71.2%, and the selectivity of 1,3-pentadiene was 87.3%. The amount of high-boiling by-products measured by the same method as in Example 1 was 0.88 g.

TABLE 6

| Component | % by weight |
|---|---|
| iso-Pentane | 8.7 |
| 3-Methyl-butene-1 | 1.5 |
| n-Pentane | 36.4 |
| Pentene-1 | 10.1 |
| 2-Methyl-butene-1 | 17.1 |
| trans-Pentene-2 | 8.1 |
| cis-Pentene-2 | 5.4 |
| 1,4-Pentadiene | 2.0 |
| 2-Methyl-butene-2 | 8.0 |
| isoprene | 0.4 |
| Cyclopentadiene | 0.9 |
| Others | 1.4 |

COMPARATIVE EXAMPLE 3

The same reaction as in Example 7 was carried out except that the comparative catalyst No. (c-3) was used. The conversion of isopentene was 46.3%. The yield of isoprene was 30.3%, and the selectivity of isoprene was 65.4%. The conversion of n-pentene was 47.1%. The yield of 1,3-pentadiene was 31.8%, and the selectivity of 1,3-pentadiene was 67.5%. The amount of high-boiling by-products was 8.68 g. During the collection of the by-products, the pipe was blocked up six times, and every time, the pipe was exchanged with a new one.

EXAMPLE 8

A catalyst (No. 35) having the composition

$$Mo_{12}Bi_1Cr_3Ni_8Al_1Fe_{0.1}K_{0.2}$$

was prepared in the same way as in Example 1 except that 37.5 g of aluminum nitrate was used instead of 26.7 g of zirconium nitrate.

One hundred milliliters of the resulting catalyst was filled in a stainless steel reaction tube having an inside diameter of 2.5 cm and a length of 60 cm, and heated to 310° C. with a metal bath. The normal butenes having the compositions shown in Table 1 were each passed through the catalyst layer so that the flow rate of the normal butenes contained therein became 18 liters per hour (gaseous, at NTP) and the flow rate of air became 132 liters per hour (at NTP). The results obtained after 3 hours from the start of the reaction are shown in Table 7.

The results given in Table 7 demonstrate that when the catalysts of this invention are used, scarcely any difference in reactivity between butene-1 and butene-2 is observed, and 1,3-butadiene is obtained in a high yield. Furthermore, even when BBRR industrially available at low cost in great quantities is used as a raw material, the same yield as in the case of using highly pure butene can be obtained. This is a very unique phenomenon. It is also seen that the amount of high-boiling by-products is small, and during the collection of the high-boiling by-products, no trouble of pipe blockage was observed with any of the materials used.

EXAMPLE 9

The catalysts (Nos. 36 to 53) shown in Table 8 were prepared in accordance with Example 8 by using various elements of the component Y instead of potassium and varying the composition of the catalyst. For phosphorus, 85% phosphoric acid was used as a raw material, and for the other elements of the component Y, the nitrates were used as raw materials. BBRR-1 shown in Table 1 was reacted in the same way as in Example 8 using each of the catalysts so prepared. The results obtained after 5 hours are shown in Table 8.

TABLE 8

| Run No. | Catalyst No. | Catalyst composition (atomic ratio) | Conversion of n-butene (%) | Yield (selectivity) of 1,3-butadiene (%) | Amount of high-boiling by-products (g) |
| --- | --- | --- | --- | --- | --- |
| 9-1 | 36 | $Mo_{12}Bi_2Cr_3Ni_8Al_2Fe_{0.1}Li_8$ | 85.9 | 77.1 (89.8) | 0.99 |
| 9-2 | 37 | $Mo_{12}Bi_{0.5}Cr_3Ni_8Al_{0.5}Fe_1Na_1$ | 85.4 | 76.8 (89.9) | 0.97 |
| 9-3 | 38 | $Mo_{12}Bi_1Cr_3Ni_8Al_1Fe_{0.2}Rb_{0.15}$ | 92.5 | 84.7 (91.6) | 0.89 |
| 9-4 | 39 | $Mo_{12}Bi_1Cr_2Ni_7Al_1Fe_2Cs_{0.05}$ | 92.1 | 84.2 (91.4) | 0.91 |
| 9-5 | 40 | $Mo_{12}Bi_1Cr_3Ni_8Al_2Fe_{0.1}Tl_{0.2}$ | 92.6 | 83.4 (90.1) | 0.98 |
| 9-6 | 41 | $Mo_{12}Bi_8Cr_{0.5}Ni_2Al_4Fe_1P_{0.5}$ | 91.0 | 82.3 (90.4) | 0.95 |
| 9-7 | 42 | $Mo_{12}Bi_1Cr_{10}Ni_1Al_1Fe_1Be_{15}$ | 82.6 | 73.1 (88.5) | 0.92 |
| 9-8 | 43 | $Mo_{12}Bi_1Cr_3Ni_3Al_8Fe_1Mg_1$ | 86.4 | 76.5 (88.5) | 0.90 |
| 9-9 | 44 | $Mo_{12}Bi_1Cr_3Ni_5Al_{0.1}Fe_5Ca_2$ | 84.7 | 75.9 (89.6) | 0.94 |
| 9-10 | 45 | $Mo_{12}Bi_2Cr_3Ni_{15}Al_1Fe_{0.1}Sr_1$ | 83.1 | 75.2 (90.5) | 0.99 |
| 9-11 | 46 | $Mo_{12}Bi_1Cr_3Ni_7Al_1Fe_{0.5}Ba_{0.5}$ | 91.1 | 84.4 (92.6) | 0.96 |
| 9-12 | 47 | $Mo_{12}Bi_1Cr_3Ni_6Al_1Fe_{0.1}Cd_2$ | 92.0 | 83.7 (91.0) | 0.93 |
| 9-13 | 48 | $Mo_{12}Bi_1Cr_3Ni_7Al_1Fe_{0.1}Zn_1$ | 91.3 | 83.3 (91.2) | 0.88 |
| 9-14 | 49 | $Mo_{12}Bi_1Cr_3Ni_5Al_1Fe_{0.1}K_{0.1}Cs_{0.01}$ | 91.6 | 83.0 (90.6) | 0.93 |
| 9-15 | 50 | $Mo_{12}Bi_1Cr_3Ni_7Al_1Fe_{0.2}Tl_{0.1}K_{0.1}$ | 93.4 | 82.8 (88.7) | 0.90 |
| 9-16 | 51 | $Mo_{12}Bi_1Cr_3Ni_7Al_1Fe_1Rb_{0.1}P_{0.5}$ | 91.9 | 82.7 (90.0) | 0.95 |
| 9-17 | 52 | $Mo_{12}Bi_3Cr_3Ni_5Al_1Fe_{0.5}K_{0.1}Cd_1$ | 92.7 | 83.1 (89.6) | 0.94 |
| 9-18 | 53 | $Mo_{12}Bi_3Cr_3Ni_7Al_1Fe_{0.1}Ba_{0.5}Be_{10}$ | 88.8 | 77.7 (87.5) | 0.91 |

TABLE 7

| Run No. | Starting hydrocarbon | Conversion of n-butene (%) | Yield (selectivity) of 1,3-butadiene (%) | Amount of high-boiling by-products (g) |
| --- | --- | --- | --- | --- |
| 8-1 | Butene-1 | 94.1 | 86.1 (91.5) | 0.92 |
| 8-2 | trans-Butene-2 | 93.7 | 85.4 (91.1) | 0.90 |
| 8-3 | cis-Butene-2 | 94.0 | 86.0 (91.5) | 0.93 |
| 8-4 | n-Butene | 94.7 | 86.6 (91.4) | 0.89 |
| 8-5 | BBRR-1 | 94.2 | 86.4 (91.7) | 0.94 |
| 8-6 | BBRR-2 | 93.1 | 85.8 (92.2) | 0.99 |

COMPARATIVE EXAMPLE 4

Comparative catalysts Nos. (c-8) to (c-14) were prepared in the same way as in Example 8 except that in the preparation of catalyst No. 35 in Example 8, the Cr, Ni, Al or Fe component was not used.

Butene-1, trans-butene-2 and BBRR-1 shown in Table 1 were each reacted in the same way as in Example 1 using each of these catalysts. The results obtained after 5 hours are shown in Table 9.

TABLE 9

| | | Reaction of butene-1 | | | Reaction of trans-butene-2 | | |
| --- | --- | --- | --- | --- | --- | --- | --- |
| Comparative catalyst No. | Catalyst composition (atomic ratio) | Conversion of butene-1 (%) | Yield (selectivity) of 1,3-butadiene (%) | Amount of high-boiling by-products (g) | Conversion of trans-Butene-2 (%) | Yield (selectivity) of 1,3-butadiene (%) | Amount of high-boiling by-products (g) |
| (c-8) | $Mo_{12}Bi_1Ni_8Al_1Fe_{0.1}K_{0.2}$ | 48.8 | 37.5 (76.8) | 4.49 | 30.1 | 23.4 (77.7) | 3.57 |
| (c-9) | $Mo_{12}Bi_1Cr_3Al_1Fe_{0.1}K_{0.2}$ | 31.0 | 25.1 (81.0) | 4.04 | 21.1 | 16.5 (78.2) | 4.41 |
| (c-10) | $Mo_{12}Bi_1Cr_3Ni_8Fe_{0.1}K_{0.2}$ | 73.6 | 60.9 (82.7) | 8.14 | 44.5 | 36.6 (82.2) | 7.71 |
| (c-11) | $Mo_{12}Bi_1Cr_3Ni_8Al_1K_{0.2}$ | 72.3 | 64.9 (89.8) | 3.98 | 71.7 | 64.2 (89.5) | 4.00 |
| (c-12) | $Mo_{12}Bi_1Ni_8Fe_{0.1}K_{0.2}$ | 70.4 | 56.4 (80.1) | 7.78 | 52.3 | 42.6 (81.5) | 7.00 |
| (c-13) | $Mo_{12}Bi_1Cr_3Ni_8K_{0.2}$ | 67.8 | 57.2 (84.4) | 6.81 | 55.6 | 46.6 (83.8) | 6.47 |
| (c-14) | $Mo_{12}Bi_1Ni_8Al_1K_{0.2}$ | 66.5 | 53.2 (80.0) | 6.33 | 45.4 | 36.0 (79.3) | 5.78 |

| | | Reaction of BBRR-1 | | |
| --- | --- | --- | --- | --- |
| Comparative catalyst No. | Catalyst composition (atomic ratio) | Conversion of n-butene (%) | Yield (selectivity) of 1,3-butadiene (%) | Amount of high-boiling by-products (g) |
| (c-8) | $Mo_{12}Bi_1Ni_8Al_1Fe_{0.1}K_{0.2}$ | 33.9 | 25.8 (76.1) | 5.71 |
| (c-9) | $Mo_{12}Bi_1Cr_3Al_1Fe_{0.1}K_{0.2}$ | 27.3 | 21.1 (77.3) | 4.48 |
| (c-10) | $Mo_{12}Bi_1Cr_3Ni_8Fe_{0.1}K_{0.2}$ | 48.8 | 40.0 (82.0) | 3.56 |
| (c-11) | $Mo_{12}Bi_1Cr_3Ni_8Al_1K_{0.2}$ | 72.1 | 65.8 (91.3) | 4.22 |

TABLE 9-continued

| | | | | |
|---|---|---|---|---|
| (c-12) | $Mo_{12}Bi_1Ni_8Fe_{0.1}K_{0.2}$ | 59.9 | 48.2 (80.5) | 8.13 |
| (c-13) | $Mo_{12}Bi_1Cr_3Ni_8K_{0.2}$ | 61.3 | 48.5 (79.1) | 7.12 |
| (c-14) | $Mo_{12}Bi_1Ni_8Al_1K_{0.2}$ | 54.7 | 43.5 (79.5) | 7.38 |

Note:
The comparative catalysts Nos. (c-10), (c-12) and (c-13) had the same compositions as the comparative catalysts Nos. (c-3), (c-5) and (c-6), respectively.

It is seen from the results that if any one of Cr, Ni, Al and Fe is lacking, the performance of the catalyst is drastically reduced, and large amounts of high-boiling by-products are formed. With the comparative catalysts other than the comparative catalyst No. (c-11), the reactivity of butene-2 is much inferior to that of butene-1, and when BBRR industrially available at low cost in large quantities is used as a raw material, no satisfactory yield of butadiene can be obtained.

In the reactions catalyzed by these comparative catalysts, the collecting pipe was blocked up more than three times during the collection of high-boiling by-products, and the reactions had to be suspended.

EXAMPLE 10

Catalysts having the composition $$Mo_{12}Bi_1Cr_3Ni_8Al_1Fe_{0.1}K_{0.2}Z_h$$

were prepared in the same way as in Example 8 except that the component Z was additionally used. For Nb and Ta, a fine powdery oxide of each was suspended in hot water and added to the solution A. For Ti, an aqueous solution of its chloride was added to the solution A. For the other elements of the component Z, an aqueous solution of the corresponding nitrate was added to the solution A.

BBRR-1 was reacted in the same way as in Example 8 using each of the catalysts prepared. The results obtained are shown in Table 10.

TABLE 10

| Run No. | Catalyst No. | Catalyst composition (atomic ratio) $Z_h$ | Conversion of n-butene (%) | Yield (selectivity) of 1,3-butadiene (%) | Amount of high-boiling by-products (g) |
|---|---|---|---|---|---|
| 10-1 | 54 | $In_{0.1}$ | 93.3 | 83.9 (89.9) | 0.62 |
| 10-2 | 55 | $Ag_1$ | 93.8 | 85.4 (91.0) | 0.82 |
| 10-3 | 56 | $Ti_5$ | 92.0 | 84.2 (91.5) | 0.82 |
| 10-4 | 57 | $Nb_{0.5}$ | 93.5 | 84.5 (90.4) | 0.80 |
| 10-5 | 58 | $Ta_{0.1}$ | 93.1 | 83.7 (89.9) | 0.77 |
| 10-6 | 59 | $Co_1$ | 92.4 | 84.3 (91.2) | 0.81 |
| 10-7 | 60 | $La_{0.1}$ | 94.4 | 82.6 (87.5) | 0.78 |
| 10-8 | 61 | $Ce_{0.5}$ | 92.9 | 83.0 (89.3) | 0.82 |
| 10-9 | 62 | $Nd_1$ | 93.0 | 84.8 (91.2) | 0.65 |
| 10-10 | 63 | $Mn_{0.5}$ | 93.4 | 85.5 (91.2) | 0.64 |
| 10-11 | 64 | $Mn_1Co_{0.5}$ | 92.7 | 84.9 (91.6) | 0.62 |
| 10-12 | 65 | $Ag_{0.1}Nd_{0.5}$ | 91.7 | 82.1 (89.5) | 0.61 |

EXAMPLE 11

The same reaction as in Example 4 was carried out except that the catalyst obtained in Example 8 was used. The conversion of n-butene contained in BBRR-1 was 94.1%. The yield of 1,3-butadiene was 85.2%, and the selectivity of 1,3-butadiene was 90.5%. The amount of high-boiling by-products collected by the same method as in Example 1 was 0.66 g.

EXAMPLE 12

The same reaction as in Example 5 was carried out except that the catalyst obtained in Example 8 was used. The conversion of n-butene was 94.4%. The yield of 1,3-butadiene was 85.6%, and the selectivity of 1,3-butadiene was 90.7%. The amount of high-boiling by-products collected by the same method as in Example 1 was 1.23 g.

EXAMPLE 13

The reaction was started as in Run No. 8-5 in Example 8, and continued for more than 100 hours to test the life of the catalyst. After the lapse of 2,000 hours, the conversion of n-butene in BBRR-1 was 93.8%. The yield of 1,3-butadiene was 86.0%, and the selectivity of 1,3-butadiene was 91.7%.

These results show that the catalyst retained substantially the same activity as in the early stage after the start of the reaction. The amount of high-boiling by-products collected was 0.87 g which was smaller than in the early stage of the reaction. During this time, the components or composition of fed BBRR-1 varied every time the material was exchanged. But the reaction proceeded always stably, and the reaction results were substantially constant.

COMPARATIVE EXAMPLE 5

The reactions of BBRR-1 in Comparative Example 4 which were catalyzed with the comparative catalysts Nos. (c-8), (c-10) and (c-11) were continued for a long period of time. With any of these catalysts, the copper pipe having an inside diameter of 8 mm at the exist of the reactor frequently blocked up with high-boiling by-products, and the operation had to be stopped after 500 hours.

EXAMPLE 14

The same reaction as in Example 7 was carried out except that the catalyst obtained in Example 8 was used. The conversion of isopentene was 76.4%. The yield of isoprene was 66.2%, and the selectivity of isoprene was 86.6%. The conversion of n-pentene was 79.7%. The yield of 1,3-pentadiene was 69.5%, and the selectivity of 1,3-pentadiene was 87.2%. The amount of high-boiling by-products measured by the same method as in Example 1 was 0.92 g.

What we claim is:

1. A process for producing a conjugated diolefin, which comprises oxidatively dehydrogenating a monoolefin having at least 4 carbon atoms in the vapor phase with molecular oxygen to form the corresponding conjugated diolefin, said reaction being carried out in the presence of a catalyst having the general composition formula $$Mo_aBi_bCr_cNi_dX_eFe_fY_gZ_hO_i$$

wherein X represents Zr or Al, Y represents at least one element selected from the group consisting of metal elements of Group Ia of the periodic table, metal elements of Group II of the periodic table, Tl and P, Z represents at least one element selected from the group consisting of In, Ag, Ti, Nb, Ta, Co, La, Ce, Nd and Mn, a, b, c, d, e, f, g, h and i are respectively the atomic numbers of Mo, Bi, Cr, Ni, X, Fe, Y, Z and O, and when a=12, b=0.05–20, c=0.05–20, d=0.1–30, e=0.01–20, f=0.01–20, g=0.001–20, h=0–20, and i is the atomic number of oxygen satisfying the atomic valences of the other elements.

2. The process of claim 1 wherein when a=12, b=0.1–8, c=0.1–10, d=1–20, e=0.05–10, f=0.05–10, g=0.01–10, h=0.01–10, and i is the atomic number of oxygen satisfying the atomic valences of the other elements.

3. The process of claim 1 wherein X is Zr.

4. The process of claim 1 wherein X is Al.

5. The process of claim 1 wherein Y is K, Rb, Cs, Tl, Ba, Zn, Cd or P.

6. The process of claim 2 wherein Z is In, Nd or Mn.

7. The process of claim 1 wherein the monolefin has 4 to 6 carbon atoms.

8. The process of claim 1 wherein the monolefin is n-butene, isopentene or n-pentene.

9. The process of claim 1 wherein the oxidative dehydrogenation is carried out at a temperature of 250° to 700° C.

10. The process of claim 1 wherein the monoolefin comprises an isomeric mixture of $C_4$ monoolefins as the main component and the conjugated diolefin is 1,3-butadiene.

11. The process of claim 1 wherein the monoolefin comprises an isomeric mixture of $C_5$ monoolefins containing isopentene, n-pentene or a mixture thereof as the main component and wherein the conjugated diolefin is isoprene, 1,3-pentadiene, or a mixture thereof, respectively.

* * * * *